United States Patent [19]

Weber

[11] Patent Number: 5,007,992
[45] Date of Patent: Apr. 16, 1991

[54] METHOD AND APPARATUS FOR REMOVING OXYGEN FROM A SEMICONDUCTOR PROCESSING REACTOR

[76] Inventor: Daniel K. Weber, 1243 Bordeaux St., Livermore, Calif. 94550

[21] Appl. No.: 351,739

[22] Filed: May 15, 1989

[51] Int. Cl.⁵ .......................... C25B 1/02; H01L 21/22
[52] U.S. Cl. .................... 204/59 R; 204/242; 204/264; 204/274; 204/291; 204/292; 501/103; 501/104; 501/126; 437/939; 437/946; 437/949
[58] Field of Search ............... 204/129, 242, 267, 274, 204/291, 130, 292, 59 R; 501/103, 104, 126; 437/939, 946, 949, 569.1

[56] References Cited

U.S. PATENT DOCUMENTS

| Re. 28,792 | 4/1976 | Ruka et al. | 204/427 |
|---|---|---|---|
| 3,400,054 | 9/1968 | Ruka et al. | 204/427 |
| 3,963,597 | 6/1976 | Kleitz et al. | 204/277 |
| 4,212,891 | 7/1980 | Fujita et al. | 426/231 |
| 4,505,790 | 3/1985 | Mase et al. | 204/130 |
| 4,530,751 | 7/1985 | Ishiguro | 204/424 |
| 4,547,281 | 10/1985 | Wang et al. | 204/424 |
| 4,725,346 | 2/1988 | Joshi | 204/427 |
| 4,786,395 | 11/1988 | Otsuka et al. | 204/409 |

FOREIGN PATENT DOCUMENTS

| 0130418 | 7/1984 | Japan | 29/569.1 |
|---|---|---|---|
| 8473923 | 11/1985 | Japan . | |
| 84188030 | 4/1986 | Japan . | |
| 8721214 | 8/1988 | Japan . | |

OTHER PUBLICATIONS

"Coupled Electrocatalysis and Gas Phase Diffusion in a Stabilized-Zirconia Tubular Flow Oxygen Pump". L. M. Rincon-Rubio et al., *J. Electrochem. Soc.*, 132(12), pp. 2919-2928, 1985.

"A Model to Predict the Removal of Oxygen from Air Using a Zirconia Solid Electrolyte Membrane". W. J. Marner et al., *Proc. Intersoc. Energy Convers. Eng. Conf.*, 23rd (vol. 2), pp. 265-271, 1988.

*Primary Examiner*—John F. Niebling
*Assistant Examiner*—Kathryn Gorgos
*Attorney, Agent, or Firm*—Townsend and Townsend

[57] ABSTRACT

A semiconductor process chamber with electrolytic ceramic cell having one major surface in the chamber. A second major surface of the cell is outside the process chamber. When activated by heat and an electric current between the two major surfaces, the cell selectively removes oxygen from the processing chamber.

20 Claims, 2 Drawing Sheets

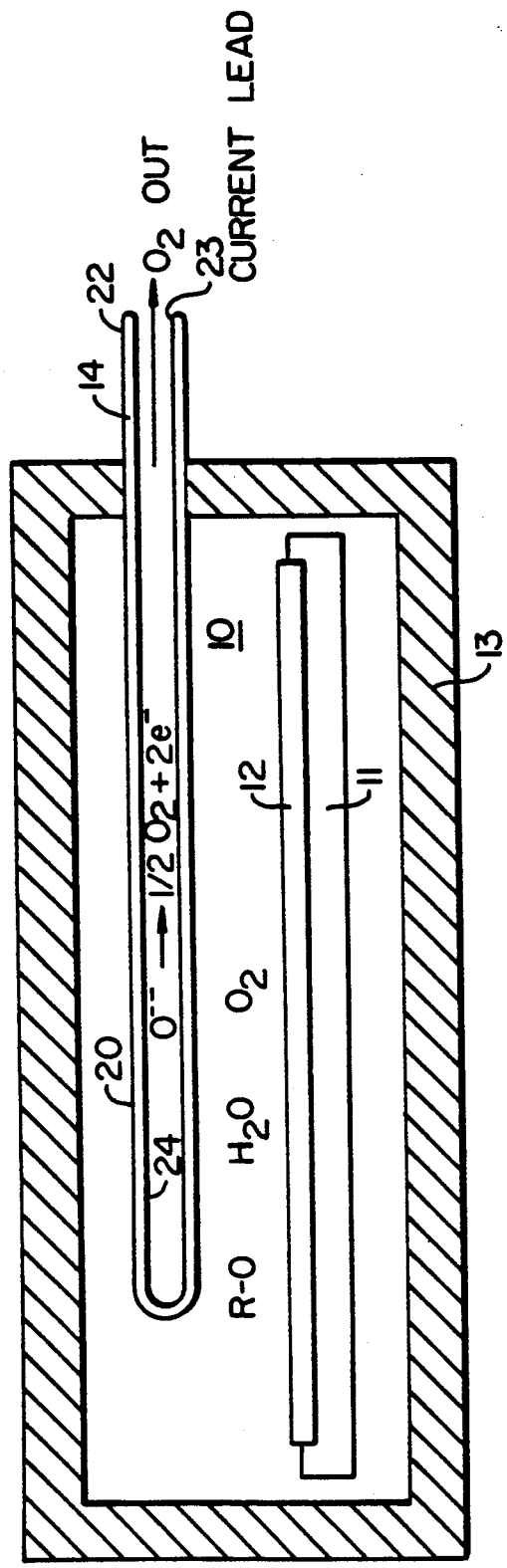
FIG._1.

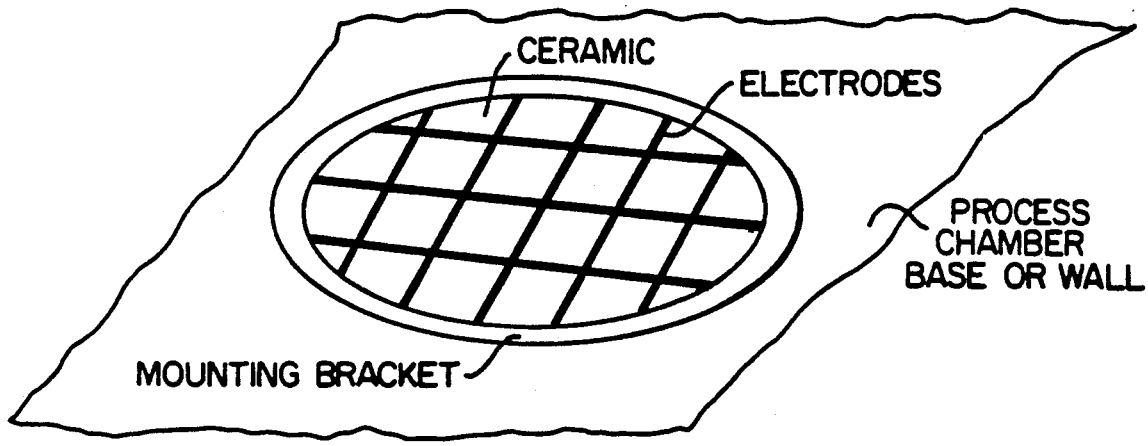
FIG._2A.
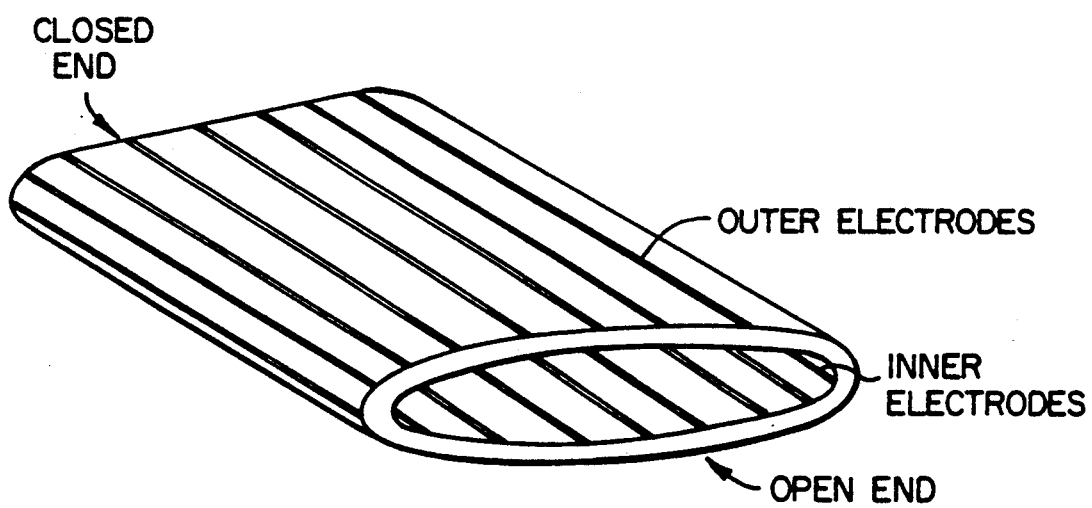
FIG._2B.

METHOD AND APPARATUS FOR REMOVING OXYGEN FROM A SEMICONDUCTOR PROCESSING REACTOR

FIELD OF THE INVENTION

This invention is related to the field of semiconductor processing and, more particularly, to techniques for removing contaminating oxygen from a semiconductor processing chamber.

BACKGROUND OF THE INVENTION

In the manufacture of semiconductor devices, a longstanding problem has been oxygen contamination. Atmospheric oxygen and water vapor still remain significant contaminants in the processing area. Oxygen readily forms unwanted oxides with the semiconductor material (e.g., silicon) to be processed and these oxides lead to imperfections in the semiconductor device. As semiconductor devices grow more complex with increasing circuit density and smaller circuit components, the effect of the oxide defects become more and more severe. The need for control over contaminating oxygen becomes critical.

Up to now a typical solution has been to flush out the process chamber to remove the ambient atmosphere from the process chamber with an inert carrier gas for a predetermined time before proceeding to the next semiconductor processing step. Of course, the problem then becomes the carrier gas purity and indeed, the purity of all process gases. These gases may then contribute unwanted oxygen to the process.

The solution to the problem of gas contamination has been to place filters or purifiers "upstream" from the process chamber to ensure the purity of source gases used in the manufacture of the semiconductor devices. Over the years various gas purification techniques based upon the principles of adsorption, absorption, chemisorption, catalytic reaction, and membrane separation have been developed to remove trace oxygen and moisture from a gas supply line. Thus the solution of flushing the ambient atmosphere from the process chamber rests upon solving the problem of gas purity.

An alternative to flushing the process chamber has been to simply remove the ambient atmosphere by low pressure (vacuum) techniques. This follows the trend in semiconductor processing toward lower process temperatures. To attain lower temperatures, control of oxides native to the processing system becomes more imperative and is generally believed to necessitate lower process pressures.

However, low pressure processing has not been completely successful and therefore pre-purified gases are often introduced into the reaction chamber to augment the effects of vacuum processing. Furthermore, lower pressures require more elaborate vacuum and pressure control equipment which add to the expense and possibilities of breakdown in the process. Processing at higher pressures (approaching ambient) is still desirable in many ways.

In addition, despite manufacturing process advances in recent years, operator error or inconsistency in the handling of semiconductor wafers, such as the loading and unloading of wafers into and out of the reactor chambers, still contributes to the oxide (moisture/oxygen) challenge regardless of the techniques used in the process chamber or the gas purification measures taken "up-stream".

To correct such errors or if the various techniques above are ineffective and the wafer is contaminated with oxides, a hydrogen purge step is performed before a particular process step is performed. Hydrogen reduces the unstable oxides formed on the wafers. However, hydrogen can be a dangerously explosive gas.

Thus, inert gas flushing, low pressure (vacuum) technology and/or the use of reducing atmospheres (hydrogen) have been only partially successful in controlling such oxides.

The present invention substantially solves or obviates many of these problems with contaminating oxygen in the processing chamber.

SUMMARY OF THE INVENTION

The present invention provides for an electrolytic, ceramic cell which has one major surface in the semiconductor processing chamber. A second major surface of the cell is outside the processing chamber. When activated by heat and an electric current between the two major surfaces, the cell selectively removes oxygen from the processing chamber.

BRIEF DESCRIPTION OF THE DRAWINGS

FIG. 1 is a cross-sectional view of one embodiment of the present invention, the processing chamber of a single-wafer epitaxial reactor with a specially adapted electrolytic ceramic cell.

FIG. 2 illustrates other shapes of electrolytic ceramic cells for different embodiments of the present invention.

DETAILED DESCRIPTION OF PREFERRED EMBODIMENTS

Broadly stated, the solution heretofore to the problem of oxygen/water vapor contamination in semiconductor processing has been to simply remove the ambient atmosphere containing unwanted oxygen from the processing chamber. This removal has been accomplished by flushing or pumping the ambient gases out.

Then "pure" gas, or gases, is/are introduced for the processing step. Elaborate filters and purifiers have been developed to guard against the reappearance of unwanted oxygen.

These problems are avoided by the present invention which focuses on the real problem of oxygen (and oxygen in water) contamination in semiconductor processing. First, it is oxygen, not the ambient atmosphere as a whole, which contaminates Semiconductor wafers. Secondly, it is unwanted oxygen in the water processing area which causes contamination. Filtered or purified gases flowing into the process area make the likelihood of oxygen contamination small, but they do not solve the problem of contamination. Finally, removal of unstable oxides on the wafer by hydrogen reduction should be avoided.

The present invention selectively removes oxygen within the process chamber of a semiconductor processing reactor. This removal of oxygen is in-situ; thus it is performed where it is needed. The result is that oxygen, water vapor and other oxygen-containing species are selectively removed from the atmosphere of the process chamber. Even unstable oxide adhering to the surface of the semiconductor substrate is removed. In general, the fugacity of oxygen is controlled.

FIG. 1 illustrates one embodiment of the present invention. A process enclosure 13 envelops a process chamber 10 of a single wafer-type, epitaxial chemical vapor deposition reactor. The chamber 10 has a susceptor 11 on which is placed the single wafer 12 upon which an epitaxial layer of semiconductor material is deposited from chemical vapors (gases).

The present invention provides for an electrolytic ceramic cell 14 in the form of a hollow cylinder with one closed end. The cell 14 is mounted in the wall of the enclosure 13 so that the closed end of the cell cylinder intrudes in the chamber 10 while the open end of the cell cylinder is outside the chamber 10. Thus the cell 14 has a major cylindrical surface 20 which is exposed to the atmosphere of the chamber 10. The cell 14 has an interior major surface 21 which is exposed to the atmosphere outside the chamber 10. Both surfaces 20, 21 are respectively covered by two electrodes (not shown) which are, in turn, connected to leads 22, 23.

The cell 14 is made of zirconia, $ZrO_2$, partially stabilized with $Y_2O_3$. This is a ceramic material with a particular property. When it is heated and an electric current is passed through the material, oxygen is transported through the material also.

This cell, being ceramic in nature, is highly resistive to harsh environments, such as that created by hydrogen chloride used to etch in process chambers. Being so stable, the cell does not shed contaminating particulates into the process chamber. Therefore, the cell is highly suitable to the ultra-clean environments required for semiconductor processing.

The electrodes cover the surfaces 20, 21 in the form of a grid or stripe. While the electrodes could cover the surfaces 20, 21 completely, it is better to have some of the area of the surfaces open so that the oxygen can pass into the zirconia ceramic directly rather than through the metal of the electrodes. A good metal for the electrodes is platinum due to its chemical inertness. It is a refractory metal and can withstand high temperatures (1200 degrees Centigrade) found in some semiconductor processes. Also platinum compounds or silver and silver compounds are preferred electrode materials due to their efficacy in oxygen ion transport.

With the metal electrodes on two surfaces of the cell, an electric DC current on the electrodes activates the cell at fairly high temperatures (typically 700° C. and above). Oxygen ions ($O^{--}$) are transported selectively through the ceramic cell walls with an intensity approaching an equivalent "selective vacuum" for oxygen of $10^{-20}$ atmospheres. What happens in the process chamber with the ceramic cell is given by the following chemical equations:

Reactions

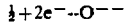

$H_2O + 2e^- \rightarrow O^{--} + H_2$ $R—O + 2e^- \rightarrow O^{--} + R$

The first equation illustrates the breakup of molecular oxygen in the chamber into ions for transport through the cell and removal away from the process chamber; the second equation shows the same for water molecules in the process chamber.

The removal of unstable oxides (R—O) formed with some compound R on the substrate is indicated by the third equation. Indeed a reactor process chamber with a ceramic cell of the present invention has been demonstrated to remove even a thick oxide film from a copper substrate while operating in an inert atmosphere at elevated temperature and ambient pressure.

The structure of the ceramic cell has $ZrO_2$ doped and partially stabilized with a compound like $Y_2O_3$. In the ceramic material, sites are created in a cubic configuration which permits the selective transport of oxygen ions. When a current (source of electrons) is applied to the $ZrO_2$ cells' electrode, oxygen ions alone pass through the porous ceramic cell.

While the cell 14 is in the form of a cylinder, other shapes could be used. One shape could be a disk as shown in FIG. 2A. In such a case the disk cell forms part of the process chamber base or wall so that one major surface faces the process chamber and the second major surface would face away from the process chamber. The advantage of a disk is that no intruding shape is required in the process enclosure which could interfere with gas flow. Furthermore, the large surface area of the cell would permit faster oxygen removal from the process chamber.

Still another shape could be a hollow wafer by extending the cross-sectional view of the cell 14 in FIG. 1 in the third or "z" axis. This shape is shown in FIG. 2B. While still extending into the process chamber 10, such a cell can remove oxygen much faster with the cell's increased surface area. Multiple cells might be used with a single process chamber, or the chamber itself could be an enlarged tube of ceramic.

Still more cell shapes can be used depending upon the requirements of the particular semiconductor process chamber and reactor. An advantage of the present invention is that the cell material is ceramic so that various shapes can be formed and sintered.

The zirconia ceramic cell mentioned above belongs to a class of electrolytic ceramic materials which selectively transport oxygen from one zone to another. These cells are at least partly characterized by a high ratio of ionic to electronic conductivity. The type of ceramic electrolytic material used is represented by the formula

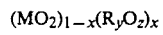

where M is one tetravalent element from the group consisting of zirconium, thorium and hafnium; R is one or more elements such as barium, calcium, lanthanum, strontium, samarium, scandium, yttrium and ytterbium; x is a small fraction, y and z are integers to make the $R_yO_z$ electrically neutral. R represents a group of elements which form +2 and +3 stable valence states in oxides. A further description of this type of ceramic cell is found in U.S. Reissue Pat. No. 28,792, reissued Apr. 27, 1976 to R. J. Ruka and J. Weissbart.

While the present invention has been mentioned in the context of a processing chamber, it is clear that the present invention also benefits an antechamber where wafers are conditioned just before processing. Furthermore, chemical vapor deposition reactors are exemplary embodiments; the present invention could be used in other semiconductor process chambers, such as in sputtering chambers and diffusion chambers where contaminating oxides are highly undesirable. Therefore, the description and illustrations above should not be construed as limiting the scope of the invention which is defined by the appended claims.

By providing for the control of semiconductor wafer surface oxide and removal of free oxygen and moisture many benefits are realized. For example:

(i) the use of low pressure processing can be minimized; many processes are now permitted to operate at or near ambient pressure;

(ii) for processes at relatively higher pressures, lower temperature processing is possible, a desireable goal;

(iii) greater safety in processing is achieved through the replacement of explosive hydrogen carrier gas with an inert gas having better thermal properties, such as nitrogen, argon or helium; and (iv) greater process repeatability, consistency and greater semiconductor product yields become possible.

While the above description provides a full and complete disclosure of the preferred embodiments of the present invention, various modifications, alternate constructions, and equivalents may be employed without departing from the true spirit and scope of the invention.

What is claimed is:

1. A reactor for processing semiconductor wafers having a reaction chamber for processing semiconductor wafers with gases, a ceramic cell having a first surface exposed to said reaction chamber and a second surface exposed away from said reaction chamber, said cell when activated removing oxygen and water from said reaction chamber through said first surface to said second surface by electrolytic action.

2. The reactor as in claim 1 wherein said ceramic cell has a high ratio of ionic to electronic conductivity.

3. The reactor as in claim 2 wherein said cell comprises zirconia.

4. The reactor as in claim 3 wherein said cell is doped with a yttrium oxide.

5. The reactor as in claim 2 wherein said cell has electrodes for receiving electric current therethrough.

6. The reactor as in claim 5 wherein said electrodes comprise platinum.

7. The reactor as in claim 2 wherein said cell is composed substantially of a material selected from the group consisting of zirconium, thorium and hafnium oxides.

8. The reactor as in claim 7 wherein said cell is at least partially stabilized with a material selected from the group consisting of barium, calcium, lanthanum, strontium, samarium, scandium, yttrium and ytterbium oxides.

9. The reactor as in claim 1 wherein said first ceramic cell surface forms part of the enclosure of said reaction chamber.

10. The reactor as in claim 9 wherein said reaction chamber enclosure comprises a base and a wall said ceramic cell mounted in said base.

11. The reactor as in claim 10 wherein said cell is the shape of a cylinder having a first closed end, said cell with said first closed end protruding into said reaction chamber, the outside surface of said cylinder forming said first surface and the inside surface of said cylinder forming said second surface.

12. The reactor as in claim 9 wherein said first ceramic cell surface forms all of the enclosure of said reaction chamber.

13. The reactor as in claim 9 further having at least a second ceramic cell having a first surface exposed to said reaction chamber and a second surface exposed away from said reaction chamber, said cell when activated removing said oxygen and water from said enclosure through said first surface to said second surface by electrolytic action.

14. A method of removing oxygen from a process enclosure of semiconductor processing reactor comprising disposing an electrolytic, ceramic cell within said enclosure such that said cell has a first surface exposed to said enclosure and a second surface removed from said enclosure;

disposing at least one semiconductor wafer in said enclosure;

activating said cell by heating said cell, and passing an electric current through said cell;

whereby said cell removes oxygen from said enclosure through said first surface and releases said oxygen to said second surface.

15. The method as in claim 14 wherein said heating step is performed as said wafers are processed in said reactor.

16. The method as in claim 15 wherein said heating step raises the temperature of said cell to above 650 degrees Centigrade.

17. The method as in claim 14 wherein said electric current is direct.

18. The method as in claim 17 wherein said current is in the general direction from one surface to the other.

19. The method as in claim 18 further comprising the step of selecting said ceramic cell composed substantially of a material from the group consisting of zirconium, thorium and hafnium oxides.

20. The method as in claim 19 further comprising the step of selecting said ceramic cell at least partially stabilized with a material from the group consisting of barium, calcium, lanthanum, strontium, samarium, scandium, yttrium and ytterbium oxides.

* * * * *